US006375944B1

(12) United States Patent
Trinchieri et al.

(10) Patent No.: US 6,375,944 B1
(45) Date of Patent: Apr. 23, 2002

(54) METHODS AND COMPOSITIONS FOR ENHANCING THE IMMUNOSTIMULATORY EFFECT OF INTERLEUKIN-12

(75) Inventors: Giorgio Trinchieri, Charly (FR); William M. F. Lee, Wynnewood; Holly Koblish, Yardley, both of PA (US)

(73) Assignees: The Wistar Institute of Anatomy and Biology; The Trustees of the University of Pennsylvania, both of Philadelphia, PA (US)

( * ) Notice: Subject to any disclaimer, the term of this patent is extended or adjusted under 35 U.S.C. 154(b) by 0 days.

(21) Appl. No.: 09/395,038

(22) Filed: Sep. 13, 1999

Related U.S. Application Data

(60) Provisional application No. 60/101,698, filed on Sep. 25, 1998.

(51) Int. Cl.[7] .......................... A61K 38/20; A61K 39/02; A61K 39/00

(52) U.S. Cl. ............................... 424/85.2; 514/2; 514/8; 514/12

(58) Field of Search ........................... 424/201.1, 203.1, 424/234.1, 85.2; 530/350

(56) References Cited

U.S. PATENT DOCUMENTS

| 5,457,038 A | 10/1995 | Trinchieri et al. | 435/69.52 |
| 5,571,515 A | 11/1996 | Scott et al. | 424/208.1 |
| 5,723,127 A | 3/1998 | Scott et al. | 424/184.1 |
| 5,976,539 A | 11/1999 | Scott et al. | 424/184.1 |

FOREIGN PATENT DOCUMENTS

| WO | WO 90/05147 | 5/1990 |
| WO | WO 94/01139 | 1/1994 |

OTHER PUBLICATIONS

Liew FY, Qing XO, Proudfoot L. Phil Trans R Soc Lond B 1997, vol. 1352, pp. 1311–1315, Cytokines and nitric oxide as effector molecules against parasitic infections.*
G. Trinchieri, "Interleukin–12: A Cytokine by Antigen–Presenting Cells With Immunoregulatory Functions in the Generation of T–Helper Cells Type 1 and Cytotoxic Lymphocytes," *Blood*, 84: 4008 (Dec. 15, 1994).
E.E. Voest et al., "Inhibition of Angiogenesis In Vivo by Interleukin 12," *J. Natl. Cancer Inst.*, 87:5813 (Apr. 19, 1995).
A. D'Andrea et al., "Production of Natural Killer Cell Stimulatory Factor (Interleukin 12) by Peripheral Blood Mononuclear Cells," *J. Exp. Med.*, 176:1387 (Nov. 1992).
G. Trinchieri, "Interleukin–12: A Proinflammatory Cytokine with Immunoregulatory Function that Bridge Innate Resistance and Antigen–Specific Adaptive Immunity," *Annu. Rev. Immunol.*, 13:251 (1995).

M.J. Brunda, "Role of IL–12 as an Anti–tumor Agent: Current Status and Future Directions," *Res. Immun.*, 146:622 (Sep.–Oct. 1995).
R.T. Gazzinelli et al., "Interleukin–12 is Required for the T–lymphocyte–Independent Induction of Interferon γ by an Intracellular Parasite and Induces Resistance in T–cell–Deficient Hosts," *Proc. Natl. Acad. Sci., USA*, 90:6115 (Jul. 1993).
G. Müller et al., "IL–12 as Mediator and Adjuvant for the Induction of Contact Sensitivity in Vivo," *J. Immunol.*, 155: 4661 (Nov. 15, 1995).
C. Sgadari et al., "Inhibition of Angiogenesis by Interleukin–12 Is Mediated by the Interferon–Inducible Protein 10," *Blood*, 87:3877 (May 1, 1996).
F.P. Heinzel et al., "Recombinant Interleukin 12 Cures Mice Infected with *Leishmania Major*," *J. Exp. Med.*, 177:1505 (May 1993).
C.M. Coughlin et al., "The Effect of Interleukin 12 Desensitization of the Antitumor Efficacy of Recombinant Interleukin 12," *Cancer Res.*, 57:2460 Jun. 15, 1997).
J.S. Orange et al., "Effects of IL–12 on the Response and Susceptibility to Experimental Viral Infections," *J. Immunol.*, 152:1253 (Feb. 1, 1994).
J. Cohen, "IL–12 Deaths: Explanation and Puzzle," *Science*, 270:908 (Nov. 10, 1995).
C.M. Coughlin et al., "Interleukin–12 and Interleukin–18 Synergistically Induce Murine Tumor Regression Which Involves Inhibition of Angiogenesis," *J. Clin. Invest.*, 101:1441 (Mar. 15, 1998).
M.B. Atkins et al., "Phase I Evaluation of Intravenous Recombinant Human Interleukin 12 in Patients with Advanced Malignancies," *Clin. Cancer Res.*, 3:409 (Mar. 1997).

(List continued on next page.)

*Primary Examiner*—Prema Mertz
*Assistant Examiner*—Sarada C Prasad
(74) *Attorney, Agent, or Firm*—Howson and Howson

(57) ABSTRACT

Methods for enhancing the therapeutic and adjuvant use of IL-12 by reducing unwanted transient immunosuppression caused by IL-12 or by high doses thereof involve co-administering IL-12 with an effective amount of an agent that inhibits or neutralizes nitric oxide (NO) in vivo. Enhanced vaccine therapy involves co-administering the IL-12 adjuvant, a selected vaccine antigen and the NO inhibiting/neutralizing agent. Additionally, the toxicity of IL-12 treatment may be reduced by co-administering IL-12 with an effective amount of the NO inhibiting or neutralizing agent. A therapeutic composition characterized by reduced toxicity in mammals contains IL-12, preferably a low dose thereof, and an NO inhibiting or neutralizing agent in a pharmaceutically acceptable carrier. A vaccine composition contains an effective adjuvanting amount of IL-12, an effective amount of an NO inhibiting or neutralizing agent, and an effective protective amount of a vaccine antigen in a pharmaceutically acceptable carrier.

18 Claims, 7 Drawing Sheets

OTHER PUBLICATIONS

H. Kurzawa et al., "Recombinant Interlleukin–12 Enhances Cellular Immune Responses to Vaccination Only after a Period of Suppression," *Cancer Res.*, 58:491 (Feb. 1, 1998).

Y.E. Noguchi et al., "Influence of Interleukin 12 on p53 Peptide Vaccination Against Established Meth A Sarcoma," *Proc. Natl. Acad. Sci.*, USA, 92:2219 (Mar. 1995).

M. Kobayashi et al., "Identification and Purification of Natural Killer Cell Stimulatory Factor (NKSF), A Cytokine with Multiple Biologic Effects on Human Lymphocytes", *J. Exp. Med.*, 170:827–845 (Sep. 1989).

C.A. Hunter et al., "Studies on the Role of Interleukin–12 in Acute Murine Toxoplasmosis," *Immunol.*, 84:16 (Jan. 1995).

S.H. Gregory et al., "Reactive Nitrogen Intermediates Supress the Primary Immunologic Response of Listeria," *J. Immunol.*, 150:2901 (Apr. 1, 1993).

M.G. Schwacha et al., "Interleukin–12 Is Critical for Induction of Nitric Oxide–Mediated Immunosupression following Vaccination of Mice with Attenuated *Salmonella typhimurium*," *Infection and Immunity*, 65:4897 (Dec. 1997).

R. Fernandez–Gomez et al., "*Trypanosoma cruzi*: Tc52 Released protein–Induced Increased Expression of Nitric Oxide Synthase and Nitric Oxide Production by Macrophages," *J. Immunol.*, 160:3471 (Apr. 1, 1998).

E. Candolfi et al., "Mitogen– and Antigen–Specific Proliferation of T Cells in Murine Toxoplasmosis Is Inhibited by Reactive Nitrogen Intermediates," *Infection and Immunity*, 62:1995 (May 1994).

K. Fecho et al., "Macrophage–Derived Nitric Oxide us Involved in the Depressed Concanavalin A Responsiveness of Splenic Lymphocytes from Rats Administered Morphine in Vivo," *J. Immunol.*, 152:5845 (Jun. 15, 1994).

J. MacMicking et al., "Nitric Oxide and Macrophage Function," *Annu. Rev. Immunol.*, 15:323 (1997).

A.M. Komarov et al., Iron Potentiates Nitric Oxide Scavenging by Dithiocarbamates in Tissue of Septic Shock Mice, *Biochim. Biophys. a.*, 1361(3):229–234 (Oct. 24, 1997).

M. Ikeda et al., "Nitric Oxide Inhibits Intracellular Adhesion Molecule–1 Expression in Rat Mesangial Cells," *J. Am. Soc. Nephrol.*, 7(10):2213–2218 (Oct. 1996).

A.K. Hughes et al., "Effects of Reactive Oxygen Species on Endothelin–1 Production by Human Mesangial Cells," *Kidney Int.*, 49(1):181–189 (Jan. 1996).

* cited by examiner

FIG.4A
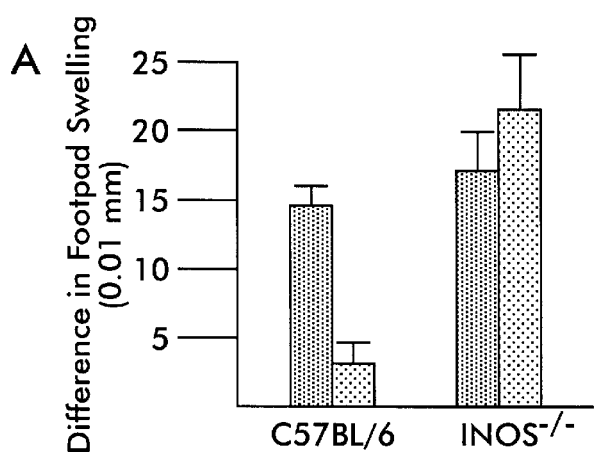
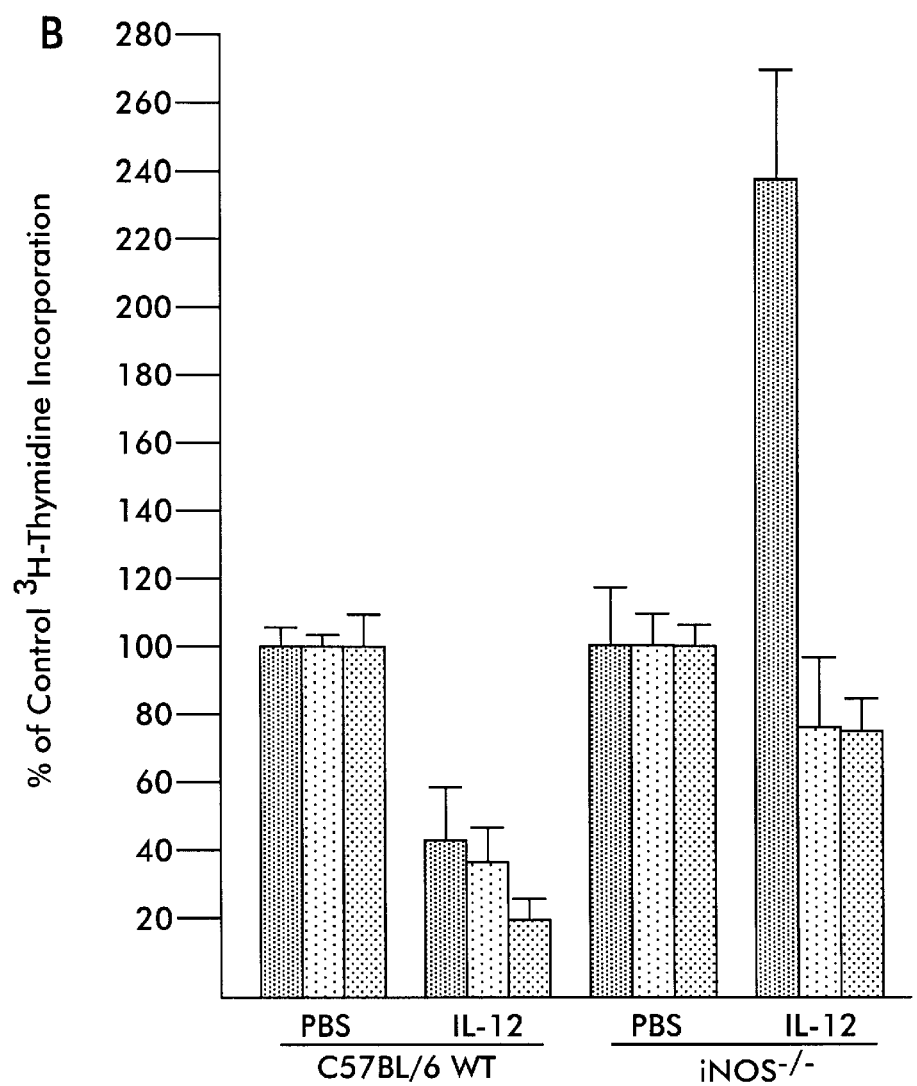
FIG.4B

METHODS AND COMPOSITIONS FOR ENHANCING THE IMMUNOSTIMULATORY EFFECT OF INTERLEUKIN-12

CROSS-REFERENCE TO RELATED APPLICATION

This application claims the benefit of U. S. Provisional Patent Application No. 60/101,698, filed Sep. 25, 1998.

This invention has been supported by grants from the National Institutes of Health, Grant Nos. CA20833, AI34412, CA10805, CA32898, CA65805, AI42334-01, and CA77851 and from the Department of the Army, Grant No. DAMD17-94-J-4027. The United States government has an interest in this invention.

FIELD OF THE INVENTION

The present invention relates generally to pharmaceutical compositions and methods of use thereof which involve using IL-12 as a therapeutic agent or an adjuvant, particularly in vaccines against cancer; and more particularly, relates to methods and compositions for enhancing IL-12 activity.

BACKGROUND OF THE INVENTION

Interleukin 12 (IL-12) is an immunoregulatory cytokine with potent antitumor, antiparasitic, antiviral and antimicrobial effects [M. J. Brunda, Res. Imm., 146:622 (1995); G. Trinchieri, Annu. Rev. Immunol., 13:251 (1995)]. Many of its activities are attributable to its ability to induce Th1 CD4+T cell differentiation, CD8+T cell cytotoxicity and natural killer (NK) cell activation. IL-12 is critical to the development of cell-mediated immunity (CMI), being a potent inducer of gamma interferon (IFNγ) from T and NK cells. IL-12 is also proinflammatory through its ability to induce production of IFNγ, tumor necrosis factor alpha (TNFα), granulocyte-macrophage colony stimulating factor (GM-CSF) and other cytokines by T and NK cells. IL-12 is required for the development of Th1 responses, is necessary for delayed type hypersensitivity (DTH) responses, and is an enhancer of NK cell cytotoxicity [G. Trinchieri, Blood, 84: 4008 (1994); G. Muller et al., J. Immunol., 155: 4661 (1995)]. Monocytes are the principal producers of IL-12 in peripheral blood mononuclear cells (PBMC), and monocyte/macrophages are thought to be the principal producing cells in vivo [Trinchieri, cited above; A. D'Andrea et al., J. Exp. Med., 176: 1387 (1992); R. T. Gazzinelli et al, Proc. Natl. Acad. Sci. U.S.A, 90: 6115 (1993)].

IFNγ is a particularly important mediator of IL-12 effects. Among other actions, IFNγ activates macrophages and induces the production of nitric oxide. IFNγ also acts on many other types of cells, including tumor cells, and its ability to upregulate MHC expression, slow cell proliferation, and inhibit angiogenesis may contribute to IL-12's antitumor effects [Voest, E. E. et al, J. Natl. Cancer Inst., 87:5813 (1995); Sgadari, C. et al, Blood, 87:3877 (1996); and Coughlin, C. M. et al, J. Clin. Invest., 101:1441 (1998)].

Therapeutic effects of IL-12 administered systemically have been reported [e.g., F. P. Heinzel et al, J. Exp. Med., 177:1505 (1993) among others]. EI-12 has also been found to be an effective adjuvant for a variety of vaccine antigens [U.S. Pat. No. 5,723,127]. However, despite its desirable therapeutic effects, the therapeutic use of recombinant IL-12 (rIL-12) can be accompanied by severe toxicities. Dose and schedule dependent toxicities have been seen during clinical trials [Atkins, M. B. et al., Clin. Can. Res., 3:409 (1997); Cohen, J., Science, 270:908 (1995)] and in mice [Coughlin, C. M. et al, Cancer. Res., 57:2460 (1997)]. Administration of rmIL-12 during LCMV infection in mice has been associated with adverse immunological effects manifested by higher viral loads, decreased anti-viral CTL activity, and poorer outcome. TNFα is implicated in rmIL-12 suppressive effects during LCMV infection [Orange, J. S. et al, J. Immunol., 152:1253 (1994)].

Further, while studying the effects of rmIL-12 in A/J mice during vaccination of genetically modified irradiated, SCK tumor cells, the present inventors observed that IL-12 transiently suppressed cellular immune responses in mice. High doses of the cytokine transiently suppressed tumor protection in vivo and proliferative responses of splenocytes to T cell mitogens in vitro [Kurzawa, H. et al, Cancer Res., 58:491 (1998)]. These effects of high-dose rmIL-12 were generalized, affecting responses to allogeneic vaccination and splenocyte mitogenic responses in naive mice of many strains, and appeared to result from impairment of immune effector function rather than failure to induce immunity.

Therapeutic applications of IL-12 may benefit from reduction or elimination of its transient immunosuppressive side effects. Approaches to reducing or eliminating IL-12 immunosuppression include using fewer doses of the cytokine. While this approach may be beneficial [Noguchi, Y. E. et al, Proc. Natl. Acad. Sci., USA, 92:2219 (1995)], finding the "proper" regime of IL-12 administration is likely to be quite involved and the results idiosyncratic. Inhibiting IFNγ action is another alternative for avoiding IL-12 immunosuppression, but is an impractical approach which is severely compromised by the fact that IFNγ may be the primary mediator of IL-12 therapeutic effects.

Thus, there remains a need in the art for methods and compositions which can eliminate the immunosuppressive effect of IL-12, particularly in situations where an enhanced and rapid adjuvant effect is desirable, and in situations where lower doses of IL-12 are desired for therapy.

SUMMARY OF THE INVENTION

In one aspect, the invention provides a method for enhancing the adjuvant effect of IL-12 comprising co-administering with IL-12 and a vaccine antigen, an effective amount of an agent that inhibits or reduces the generation of, or that breaks down, absorbs, metabolizes or eliminates, nitric oxide in vivo (hereafter referred to as "nitric oxide inhibiting and/or neutralizing agent"). The vaccine antigen may be a mammalian tumor cell antigen or an antigen from a pathogenic microorganism.

In another aspect, the invention provides a method for reducing the immunosuppressive effects of IL-12 treatment comprising co-administering with IL-12, an effective amount of the nitric oxide inhibiting and/or neutralizing agent described above.

In another aspect, the invention provides a method for reducing the toxicity of IL-12 treatment comprising co-administering with an effective dose of IL-12, an effective amount of a nitric oxide inhibiting and/or neutralizing agent. The effective dose of IL-12 may be a low dose thereof.

Still another aspect of the invention is a therapeutic composition comprising IL-12, characterized by reduced toxicity in mammals, which comprises IL-12, preferably a low dose thereof, and an effective amount of a nitric oxide inhibiting and/or neutralizing agent in a pharmaceutically acceptable carrier.

In yet a further aspect, the invention provides an adjuvant composition suitable for use with a vaccine antigen comprising an effective adjuvanting amount of IL-12 and an effective amount of a nitric oxide inhibiting and/or neutralizing agent in a pharmaceutically acceptable carrier.

In still a further aspect, the invention provides a vaccine composition comprising an effective adjuvanting amount of IL-12, an effective amount of a nitric oxide inhibiting and/or neutralizing agent and an effective protective amount of a vaccine antigen in a pharmaceutically acceptable carrier.

Other aspects and advantages of the present invention are described further in the following detailed description of the preferred embodiments thereof.

BRIEF DESCRIPTION OF THE DRAWINGS

FIG. 4A is a bar graph illustrating mean footpad swelling (+S.E.) from 3 mice/treatment group for mice rendered genetically deficient in inducible nitric oxide synthase (iNOS), i.e. iNOS–/– mice, and wild-type C57BL/6 mice vaccinated with irradiated HKB cells and given rmIL-12 (gray bars) or PBS (black bars) injections. Footpad injections for DTH assessment were performed on day 12, and swelling measured 24 hours later.

FIG. 4B is a bar graph illustrating the percentage of thymidine incorporation for mitogenic stimulation (Con C: black bars; IL-12: hatched bars) and allogeneic stimulation (stippled bars) of splenocytes, performed as described in FIGS. 2A, 2B, 3A and 3B above.

BRIEF DESCRIPTION OF THE INVENTION

Figure 1A:
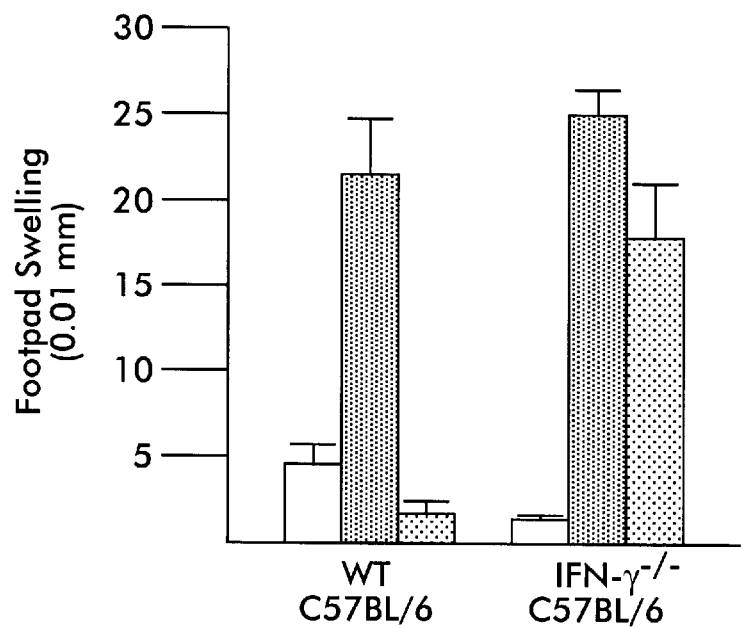
FIG. 1A is a bar graph which reports mean footpad swelling (+standard error or S.E.) for C57BL/6 mice genetically deficient for IFNγ and wild-type control mice which are (a) unvaccinated (open bars; 2 mice); (b) vaccinated with HKB cells and given phosphate buffered saline (PBS; black bars; 4 mice); (c) vaccinated with HKB cells and given recombinant murine Interleukin-12 (rmIL-12) on days 0–4 and 7–11 (gray bars; 4 mice). All mice were challenged with irradiated SCK cells in the right foot, and with PBS control injection in the left foot on day 12.

The present invention provides a solution to the unfilled need in the art for methods and compositions which enhance the therapeutic and adjuvant use of IL-12. The inventors provide herewith both methods and compositions for reducing and/or eliminating the suppression of cellular immune response caused by administration of recombinant interleukin 12 (rIL-12), particularly where IL-12 is employed as a vaccine adjuvant in mammalian patients, preferably humans. Moreover, the present invention also provides methods and compositions for enhancing the biological activity of IL-12, in therapeutic treatment of mammalian patients based on overcoming the cause of the unwanted suppression which has previously led to the use of more toxic doses of IL-12 in clinical trials of disease treatment.

I Mechanism of the Invention

As discovered by the inventors in the course of the work discussed in the examples below, recombinant IL-12, when administered to mammals undergoing alloimmunization, has been found to transiently, but profoundly, suppress in vivo and in vitro allogeneic responses and in vitro splenocyte mitogenic responses. In vivo and in vitro evidence indicates that neutralizing anti-IFNγ antibodies, but not anti-TFNα, nor antibodies to other cytokines, can prevent rIL-12-induced suppression (see Examples 1 and 2 below. The importance of the role of IFNγ in this immune suppression is demonstrated by splenocyte fractionation studies in IFNγ$^{-/-}$ and IFNγR1$^{-/-}$ mice which are not immunosuppressed by rIL-12, which reveal that adherent cells from rIL-12 treated mice suppress the mitogenic response of normal nonadherent cells to Conconavalin A (ConA) and IL-12.

The inventors have determined that the mechanism of rIL-12 immune suppression results from inhibition of T cell proliferation by nitric oxide (NO) generated by macrophages activated by the IFNγ produced in response to rIL-12. Experiments using splenocyte fractionation, an inhibitor of NO generation, and mice genetically deficient in inducible nitric oxide synthase (iNOS–/– mice) revealed that adherent cells of the spleen, through stimulated production of NO by nitric oxide synthase (NOS) are responsible for suppressing T cell mitogenesis in vitro and cellular immune responses in vivo. Having thus identified the mechanism, the inventors found that addition of an inhibitor of NOS restored mitogenic responses, and iNOS$^{-/-}$ mice were not immunosuppressed by IL-12. These results demonstrate that suppression of T cell responses were due to NO produced by macrophages activated by high levels of IFNγ induced by rIL-12.

When inhibitors of nitric oxide generation were given with rIL-12 during vaccination of animals with irradiated tumor cells, immunosuppression was averted and the ability of rIL-12 to enhance induction of protective antitumor immunity was revealed, demonstrating that rIL-12 is an effective vaccine adjuvant whose efficacy may be initially masked by its transient immunosuppressive effect.

Without being bound by theory, the inventors believe that events leading to immune suppression by rIL-12 administration (particularly high dosage IL-12 administration) are initiated by its induction of IFNγ production by host lymphocytes. Levels of IFNγ production high enough to activate macrophages and induce NOS activity generate high levels of NO which impairs the proliferation of T cells in response to mitogens. That adherent cells rather than T cells are primarily responsible for the pathogenesis of rIL-12 immune suppression is supported by the fact that T cells from the spleens of rIL-12-treated mice are normally mitogenic when cocultured with adherent cells from normal mice or from rIL-12 -treated iNOS–/– mice. Impairment is transient presumably because T cell proliferative responses recover as IFNγ production and consequent macrophage activation wanes following completion of rIL-12 therapy.

The identification of NO as a mediator of rIL-12-induced immunosuppression is consistent with its known activities. NO, a key component of host defense mechanisms against invading pathogens, is produced by NOS in macrophages activated by IFNγ and other cytokines [MacMicking, J. et al, *Annu. Rev. Immunol.*, 15:323 (1997)]. Impaired splenocyte mitogenesis during *Salmonella typhimurium, Trypanasoma cruzi, Toxoplasma gondii* and *Listeria monocytogenes* infections is due to NO production associated with high levels of IFNγ, endogenous IL-12 and other proinflammatory cytokines [Hunter, C. A. et al, *Immunol.*, 84:16 (1995); Gregory, S. H. et al, *J. Immunol.*, 150:2901 (1993); Schwacha, M. G. et al, *Infection and Immunity*, 65:4897 (1997); and Fernandez-Gomez, R. et al, *J. Immunol.*, 160:3471 (1998)]. When splenocytes from these mice are fractionated, the adherent population containing macrophages and producing nitric oxide appears to suppress splenic T cell mitogenic responses, and this suppression is reversed by inhibitors of NOS [Candolfi, E. et al, *Infection and Immunity*, 62:1995 (1994)]. Thus, diverse processes that induce NO production of macrophages [Hunter, cited above; Gregory, cited above; and Fecho, K. et al, *J. Immunol.*, 152:5845 (1994)] can impair T cell proliferative responses.

Based on the inventors' discovery, to this list of processes that induce NO production can now be added rIL-12 (including, for example, high doses of IL-12) which, through induction of high levels of IFNγ and in the absence of additional inflammatory stimuli, sufficiently activates macrophages to induce immunosuppression.

II Methods of the Invention

Therefore according to the present invention the therapeutic and vaccine adjuvant use of IL-12 can be enhanced by eliminating or reducing its transient immunosuppressive effects, which normally occur due to administration of recombinant IL-12. This elimination or reduction of the unwanted immunosuppressive effects of IL-12 can be accomplished by co-administering with IL-12 an effective amount of an agent which can retard or prevent nitric oxide synthesis in vivo by macrophages in response to IFNγ stimulation. Alternatively, this elimination or reduction of the unwanted immunosuppressive effects of IL-12 can be accomplished by co-administering with IL-12 an effective amount of an agent which can break down, absorb, metabolize, eliminate or "neutralize" the immunosuppressive activity of NO in vivo. For ease of reference, these agents are referred to collectively as "NO inhibiting and/or neutralizing agents".

For example, the adjuvant effect of IL-12 when administered with a selected vaccine antigen, e.g., a mammalian tumor cell antigen or an antigen from a pathogenic microorganism (see e.g., U.S. Pat. No. 5,723,127), may be enhanced by co-administering to a mammalian patient the IL-12, the vaccine antigen, and an effective amount of an NO inhibiting and neutralizing agent. Such co-administration may include simultaneously administering the NO inhibiting and/or neutralizing agent with IL-12 and the antigen. Alternatively, co-administration may involve sequentially administering the NO inhibiting and neutralizing agent, the IL-12 and the antigen in any desired order. For example, it is desirable to administer IL-12 before the vaccine composition, e.g., about one or more days before the vaccine. As another example, the NO inhibiting and/or neutralizing agents can be administered after the IL-12 is administered but, preferably before the gamma interferon is induced, e.g., within 2 to 24 hours thereafter. More preferably, to enhance the IL-12 adjuvant effect, the NO inhibiting and/or neutralizing agent is administered within about one to about two hours after the IL-12 and preferably with the vaccine antigen administration. Other orders of administration may readily be selected by one of skill in the art.

In still another embodiment of the present invention, a method for reducing the immunosuppressive effects of IL-12 when the IL-12 is used therapeutically comprises co-administering with IL-12, an effective amount of an NO inhibiting and neutralizing agent of this invention. Such co-administration may include simultaneously administering the inhibitor with IL-12. Alternatively, co-administration may involve sequentially administering the NO inhibiting and neutralizing agent and the IL-12 in any desired order. Preferably, to enhance the IL-12 therapeutic effect, the NO inhibiting and/or neutralizing agent is administered within about 2 hours of the IL-12. This method is useful with the currently employed "high doses" of IL-12 which have been used in clinical trials of therapeutic treatment with IL-12. Still another desirable embodiment of this aspect of the invention enables one to reduce the toxicity of IL-12 treatment by co-administering an effective amount of an NO inhibiting and/or neutralizing agent with a "low dose" of IL-12. The co-administration of the NO inhibiting and/or neutralizing agent with a dose of IL-12 which may currently be considered suboptimal to accomplish the desired biological effects of IL-12 treatment (i.e., a dose comprises between about 10 to about 200 ng IL-12 per kg body weight, and preferably between about 50 to about 100 ng/kg) is anticipated to enhance the IL-12 effect. The method of the present invention enables the use of the low doses of IL-12 in therapy, which will reduce the toxic side effects noted with the currently employed high doses (about 100–1000 ng/kg).

To perform the above defined methods of this invention, the following components are needed, i.e., IL-12, the NO inhibiting and/or neutralizing agent, and optionally, the vaccine antigen.

A. Interleukin 12

Interleukin-12 (IL-12), originally called natural killer cell stimulatory factor, is a heterodimeric cytokine described, for example, in M. Kobayashi et al, *J. Exp. Med.,* 1709:827 (1989) and in U.S. Pat. No. 5,457,038, and in the related published International Patent Application WO90/05147 and European patent application No. 441,900. The expression and isolation of IL-12 protein in recombinant host cells, the DNA and amino acid sequences of the 30kd and 40kd subunits of the heterodimeric human IL-12 are provided in the above recited documents, incorporated herein by reference. Research quantities of recombinant human and murine IL-12 are also available from Genetics Institute, Inc., Cambridge, Mass.

Fragments of IL-12 which share the same biological activity of the full-length protein as well as the DNA sequences which encode IL-12 or fragments thereof may also be employed as the IL-12 of the compositions. Such biologically active fragments may be obtained by conventional recombinant engineering methods of fragmenting a protein. Any fragment may be readily assessed for IL-12 biological activity by testing in an assay which measures the induction of interferon-γ secretion by human lymphocytes [M. Kobayashi et al, *J. Exp. Med.,* 1709:827 (1989)]. It should be understood by one of skill in the art, that such identification of suitable biologically active fragments of IL-12 for use in the composition of this invention involves only a minor amount of routine experimentation.

For use in the methods and compositions of this invention, IL-12 may be employed as biologically active heterodimeric protein or peptide fragments. Where it is used throughout the examples, the term IL-12 refers to the heterodimeric protein unless smaller fragments thereof are specifically identified.

Based on clinical trials and other experiments, the therapeutic dosages of IL-12 that are now in use, and which have been reported to cause toxic side effects range from about 100 to 500 ng or more IL-12 protein/kg patient body weight. "Low doses" of IL-12 protein which have previously shown minimal therapeutic benefit, but which may be used according to this invention range from between about 10 to 100 ng IL-12 protein per kg patient body weight.

When used as an adjuvant for a selected vaccine composition containing an antigen, the dosage amounts will depend upon the cancer or pathogen for which the vaccine is designed, the nature of the antigen, the dosage amounts of the antigen as well as the species and physical and medical conditions (e.g., general healthy, weight, etc.) of the vaccinate. As one example, an effective adjuvanting dosage or amount of IL-12 protein is desirably between about 0.1 µg to about 0.1 mg of IL-12 protein per about 25 µg of antigen. In view of this teaching, one of skill in the art will know that the adjuvanting amount of IL-12 for any particular vaccine will be readily defined by balancing the efficacy and toxicity of the IL-12 and antigen combination with the IL-12 enhancing effect of the NO inhibiting and/or neutralizing agent. One of skill in the art of vaccine composition is expected to be able to readily determine suitable amounts of IL-12 to adjuvant particular vaccines.

Therapeutic administration of IL-12 protein or peptide may take any route of administration and such routes as e.g., subcutaneous, intraperitoneal, oral, intramuscular, intravascular, intranasal, etc., may be used for therapeutic or vaccine administration. When it is administered as an adjuvant with a vaccine composition, IL-12 is administered by the same route as the vaccinal antigen.

Still another mode of delivering IL-12 to the mammalian patient as an adjuvant or as a therapeutic is in the form of DNA. Nucleic acid delivery compositions and methods are known to those of skill in the art and may be employed rather than administration of the IL-12 protein, as desired. IL-12 may be employed in the methods of this invention or in the compositions described herein as DNA sequences, either administered as naked DNA, or associated with a pharmaceutically acceptable carrier and provide for in vivo expression of the IL-12 protein or peptide. So-called 'naked DNA' may be used to express the IL-12 protein or peptide fragment in vivo in a patient. [See, e.g., J. Cohen, *Science,* 259:1691–1692 (Mar. 19, 1993); E. Fynan et al, *Proc. Natl. Acad. Sci.,* 90: 11478–11482 (Dec. 1993); J. A. Wolff et al, *Biotechniques,* 11:474–485 (1991) which describe similar uses of 'naked DNA', all incorporated by reference herein]. For example, IL-12 DNA for use as an adjuvant may be incorporated, or transduced, into a pathogenic microorganism itself, if the whole pathogen itself is to be employed as the vaccinal antigen. Alternatively, IL-12 DNA may be administered therapeutically or as part of the vaccine composition e.g., by injection.

Alternatively, IL-12 DNA may be administered as part of a vector or as a cassette containing the IL-12 DNA sequences operatively linked to a promoter sequence. See, e.g., International Patent Application PCT WO94/01139, published Jan. 20, 1994. Briefly, the DNA encoding the IL-12 protein or desired fragment thereof may be inserted into a nucleic acid cassette. This cassette may be engineered to contain, in addition to the IL-12 sequence to be expressed, other optional flanking sequences which enable its insertion into a vector. This cassette may then be inserted into an appropriate DNA vector downstream of a promoter, an mRNA leader sequence, an initiation site and other regulatory sequences capable of directing the replication and expression of that sequence in vivo. This vector permits infection of vaccinate's cells and expression of the IL-12 in vivo.

Numerous types of appropriate vectors are known in the art for protein expression and may be designed by standard molecular biology techniques. Such vectors are selected from among conventional vector types including insects, e.g., baculovirus expression, or yeast, fungal, bacterial or viral expression systems. Methods for obtaining such vectors are well-known. See, Sambrook et al, *Molecular Clon-* ing. A Laboratory Manual, 2d edition, Cold Spring Harbor Laboratory, New York (1989); Miller et al, *Genetic Engineering*, 8:277–298 (Plenum Press 1986) and references cited therein. Recombinant viral vectors, such as retroviruses or adenoviruses, are preferred for integrating the exogenous DNA into the chromosome of the cell.

Also where desired, the regulatory sequences in such a vector which control and direct expression of the IL-12 gene product in the transfected cell include an inducible promoter. Inducible promoters are those which "turn on" expression of the gene when in the presence of an inducing agent. Examples of suitable inducible promoters include, without limitation, the sheep metallothionine (MT) promoter, the mouse mammary tumor virus (MMTV), the tet promoter, etc. The inducing agents may be a glucocorticoid such as dexamethasone, for, e.g., the MMTV promoter, or a metal, e.g., zinc, for the MT promoter; or an antibiotic, such as tetracycline for tet promoter. Still other inducible promoters may be selected by one of skill in the art, such as those identified in International patent application WO95/13392, published May 18, 1995, and incorporated by reference herein. The identity of the inducible promoter is not a limitation of this invention.

When IL-12 nucleic acid sequences are employed as the therapeutic agent or adjuvant either as 'naked DNA' operatively linked to a selected promoter sequence or transduced into a strain of the pathogenic microorganism, rather than the protein itself, the amounts of DNA to be delivered and the routes of delivery may parallel the IL-12 protein amounts for adjuvant or therapeutic delivery described above and may also be determined readily by one of skill in the art.

The IL-12 useful in the form of protein, peptide or nucleic acids and fragments thereof may be produced by now-conventional synthetic or recombinant methods. See, e.g., conventional texts such as Sambrook et al, "Molecular Cloning. A Laboratory Manual", $2^{nd}$ edition, Cold Spring Harbor Laboratory, Cold Spring, N.Y. (1989). Alternatively, IL-12 may be purchased from pharmaceutical companies.

B. Agents that Interfere with NO Generation and/or Neutralize its Activity In Vivo Another component useful in the methods and compositions of this invention are agents that either inhibit NO generation by macrophages, or agents that neutralize NO activity in vivo. Among such agents useful in the methods and compositions of the present invention are inhibitors of the enzyme nitric oxide synthase (NOS). Agents which inhibit the enzyme NOS include the following: $N^G$-monomethyl-L-arginine (L-NMMA) (Sigma) and $N^\omega$-nitro-L-arginine methyl ester (L-NAME) (Sigma). The ideal inhibitor would be one effective selectively for inducible NOS, and not for other constitutive NOS enzymes. See, for example, those compounds listed in Table 3 of J. E. Ogden and P. K. Moore, *Trends Biotechnol.*, 13:70–78 (1995), including, without limitation, L-$N^G$ monomethyl arginine (L-NMMA), L-$N^G$ nitroarginine (L-NORAG), L-$N^G$ nitroarginine methylester (L-NAME), L-$N^G$ nitroarginine p-nitroanilide (L-NAPNA), L-$N^G$ aminoarginine (L-NAA), L-$N^G$ cyclopropylarginine, L-$N^G$ allylarginine, asymmetric L-$N^G N^G$ dimethylarginine (L-ADMA), L-$N^\omega$ iminoethyl ornithine (L-NIO), 7-nitro indazole (7-NI), 2,7 dinitro indazole, 3-bromo 7-nitro indazole, aminoguanidine, N,N'-diaminoguanidine, dimethylguanidine, diphenyleneiodonium, iodoniumdiphenyl, di-2-thienyliodonium, chlorpromazine, trifluoperazine, pimozide, clozapine, calmidazolium, 2,4 diamino-6-hydroxypyrimidine, methotrexate, N-acetyl-5-hydroxytryptamine, miconazole, ketoconazole, clotrimazole, imidazole, 1-, 2- and 4-phenylimidazole, methylene blue, NO, carbon monoxide, ebselen, phencyclidine, and antineoplastic agents (doxorubicin, aclarubicin). One of skill in the art provided with this specification and with knowledge conventional in the art is expected to readily select the appropriate agent for use in the various aspects of this invention.

Agents which breakdown, absorb, eliminate, metabolize or scavenge (i.e., neutralize) NO may also be employed in the methods and compositions of this invention. Such agents include dithiocarbamates, such as diethyldithiocarbamate, pyrrolidinedithiocarbamate, N-methyl-D-glucamine dithiocarbamate [A. M. Komarov el al, *Biochim. Biophys Acta*, 1361(3):229–234 (1997)] and hemoglobin [M. Ikeda et al, *J. Am. Soc. Nephrol.*, 7(10):2213–2218 (1996)]. Some reactive oxygen species scavengers may also be similarly useful [A. K. Hughes et al, *Kidney Int.*, 49(1):181–189 (1996)].

These NO inhibiting and/or neutralizing agents may be safely administered to a mammalian patient in dosages of from about 0.1 mg/kg to about 50 mg/kg. Other safe dosages may be selected from a review of the art on any particular agent. They may be administered simultaneously with the IL-12, before the IL-12 or after the IL-12 when used to enhance therapeutic IL-12 effects. The NO inhibiting and/or neutralizing agents may also be administered in any order, i.e., with, before or after, the IL-12 and the vaccine antigen, where IL-12 is being employed as a vaccine adjuvant. If IL-12 is administered as DNA, the inhibitor may be needed at a later time.

The NO inhibiting and/or neutralizing agents identified above may be obtained commercially, for example, from Sigma Corporation or other companies. Alternatively the peptide or protein NO inhibiting and/or neutralizing agents or these agents in nucleic acid form may be prepared synthetically or recombinantly, as described above for the IL-12.

C. The Vaccine Antigen

Where the IL-12 is administered as an adjuvant, the vaccine antigen may be a cancer antigen, such as a mammalian tumor cell surface antigen, or a cancer cell transfected with, and capable of expressing, a selected antigen, e.g., B7.

Alternatively, the vaccine antigen may be obtained from pathogenic microorganisms (e.g., bacteria, protozoa, helminths, viruses and parasites) which are the causative agents of diseases such as HIV, Hepatitis A, Hepatitis B, Hepatitis C, rabies virus, poliovirus, influenza virus, meningitis virus, measles virus, mumps virus, rubella, pertussis, encephalitis virus, papilloma virus, yellow fever virus, respiratory syncytial virus, parvovirus, chikungunya virus, haemorrhagic fever viruses, Klebsiella, and Herpes viruses, particularly, varicella, cytomegalovirus and Epstein-Barr virus, leprosy and tuberculosis, leishmaniasis and malaria or schistosomiasis. This list is not inclusive and one of skill in the art would understand that one could expand this list to include an antigen from any pathogenic organism which may be useful in a vaccine.

Such vaccine antigens may be prepared as is known to one of skill in the art of vaccine preparation by several means, for example, synthetically or recombinantly, as described above for the IL-12, depending on the identity of the antigen, or the antigens may be naturally isolated from the pathogen.

Such antigens may be administered as whole killed organisms, or as heat- or chemically-inactivated organisms or portions thereof, or produced as DNA as discussed above in detail for IL-12.

III. Compositions of the Invention

Based on the above disclosures, the present invention also encompasses several forms of pharmaceutical compositions containing the IL-12 and NO inhibiting and/or neutralizing agents, and optionally the vaccine antigen.

Thus, as one embodiment the invention provides a therapeutic composition comprising a therapeutically effective amount of IL-12 and an effective amount of an NO inhibiting and/or neutralizing agent in a pharmaceutically acceptable carrier. As discussed above, such a therapeutically effective dosage of IL-12 in this composition may include the higher dosages of current clinical trials. More preferably, the composition uses lower doses of IL-12 and is characterized by a lower toxicity for mammalian, preferably human, patients. Such as composition may optionally contain other pharmaceutical ingredients which are known to one of skill in the pharmaceutical art to provide timed delivery, or provide coatings, stabilizers, preservatives, etc. to the active ingredients.

In still another embodiment, the invention provides an adjuvant composition suitable for use with a vaccine antigen, which comprises an effective adjuvanting amount of IL-12 and an effective amount of an NO inhibiting and/or neutralizing agent in a pharmaceutically acceptable carrier. Yet another composition of the invention is a vaccine composition comprising an effective adjuvanting amount of IL-12, an effective amount of an NO inhibiting and/or neutralizing agent, and an effective protective amount of a vaccine antigen in a pharmaceutically acceptable carrier.

These compositions can contain each component as a peptide or protein or chemical pharmaceutical compounds, in dosages as described above in Part II.

Alternatively, these compositions may contain the components as nucleic acids, as described above. The IL-12 and NO inhibiting and/or neutralizing agent, and optionally the vaccine antigen, as DNA, may be incorporated, or transduced, into one or multiple DNA molecules, i.e., plasmid vectors, of which many types are known, or into one or more viral vectors, preferably poxvirus or adenovirus vectors, for delivery of the IL-12, NO inhibiting and/or neutralizing agent, and optional vaccine antigen DNA into the patient. When incorporated into another DNA molecule, the DNA sequence encoding the IL-12 and/or NO inhibiting and/or neutralizing agent, and/or vaccine antigen is operatively linked with regulatory sequences which direct the expression of the encoded protein or fragment in vivo. Briefly, a cassette may be engineered to contain, in addition to the IL-12 and/or NO inhibiting and/or neutralizing agent and/or vaccine antigen sequence to be expressed, other flanking sequences which enable insertion into a vector. This cassette may then be inserted into an appropriate DNA vector downstream of a promoter, an mRNA leader sequence, an initiation site and other regulatory sequences capable of directing the replication and expression of the desired component sequence(s) in a host cell.

When administered as naked DNA or as part of plasmid or viral vectors, the sequences encoding IL-12, the NO inhibiting and/or neutralizing agent and the optional vaccine antigen may be present on separate DNA molecules which are admixed for administration, or may be assembled as part of a single polycistronic molecule, under the control of the same or different regulatory sequences.

For either the protein compositions or DNA compositions described above, suitable pharmaceutically acceptable carriers can facilitate administration of proteins, DNA or chemical compounds but are physiologically inert and/or nonharmful. Carriers may be selected by one of skill in the art. Exemplary carriers include sterile saline, lactose, sucrose, calcium phosphate, gelatin, dextrin, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used. Optionally, this composition may also contain conventional pharmaceutical ingredients, such as preservatives, or chemical stabilizers.

Alternatively, or in addition to the compounds of the invention, other agents useful in treating cancer, or useful in treating any accompanying bacterial or viral infection, e.g., antivirals, or immunostimulatory agents and cytokine regulation elements, or costimulatory molecules, such as B7, are expected to be useful in the components of this invention. Such agents may operate in concert with the therapeutic compositions of this invention and may be delivered to the patient as DNA or protein, or as a conventional pharmaceutical synthetic agent. The development of therapeutic compositions containing these agents is within the skill of one in the art in view of the teachings of this invention.

The dosages of the components of these compositions are discussed above with respect to the methods of administration.

The following examples illustrate various aspects of this invention and do not limit the invention, the scope of which is embodied in the appended claims. The animals identified below are employed in the following examples: female C57BL/6 (H-$2^b$) mice, 5–8 weeks old [Harlan-Sprague-Dawley (Indianapolis, Ind.)]; IFNγ$^{-/-}$ and iNOS$^{-/-}$ C57BL/6 mice and wild-type controls and female A/J (H-$2^a$) mice, 5–8 weeks old [Jackson Laboratories (Bar Harbor, Me.)]; IFNγR1$^{-/-}$ C57BL/6×SV129 mice and controls (stemmed from a breeding pair that was a gift from Dr. Michel Aguet) [Huang, S. et al, Science, 259:1742 (1993)]. TNFαp55 and p75 receptor$^{-/-}$ C57BL/6×SV129 mice and controls were provided by Dr. Phillip Scott and Michelle Nashleanas (University of Pennsylvania, Philadelphia, Pa.) with permission from Genentech (South San Francisco, Calif.) and Dr. Horst Bluethmann and Roche (Basel, Switzerland) [Kalb, A. et al., *J. Biol. Chem.,* 271:28097 (1996); Rothe, J. et al, *Nature.* 364:798 (1993)].

Where the examples below refer to HKB cells, such cells were established from a spontaneous tumor that arose in an aged, unmanipulated female A/J mouse and maintained in RPMI with 10% fetal calf serum (FCS) and penicillin/streptomycin. They are MHC class I+ and nontumorigenic in A/J mice when $10^6$ cells are injected simultaneously (sc). SCK murine mammary carcinoma cells and SCK.GM cells were described in Kurzawa, H, cited above.

EXAMPLE 1

IFNγ Mediates rIL-12 Induced Immunosuppression

To understand the mechanisms underlying this suppression without the confounding influence of tumor burden or infection with pathogens, the effects of rIL-12 on allogeneic immune responses were observed. In vivo and in vitro evidence indicates that alloimmunization is transiently but profoundly suppressed by high-dose rIL-12. It seems to impair immune effector mechanisms, because responses in mice with established immunity are also suppressed. It does not appear to impair induction of immunity, since rIL-12 given during tumor cell vaccination provides enhanced protective antitumor immunity after the period of immunosuppression. rIL-12 impairment of cellular immune responses is consistently associated with and likely due to impaired T cell mitogenic responses. The roles of IFNγ and TNFα were examined in rmIL-12 induced suppression of responses to alloimmunization in the following experiments:

A. C57BL/6 (H-$2^b$) mice were vaccinated with irradiated allogeneic HKB (H-$2^a$) cells suspended in PBS at $10^7$ trypan blue-excluding cells/ml. Cells were irradiated with 6000 rads from a $^{137}$Cs source, and mice were vaccinated with $10^6$ cells s.c. (day 0). Mice were given rmIL-12 (Genetics Institute, Andover, Mass.) by intraperitoneal injection (ip) with 500 ng/day on days 0–4 and 7–11 (10 injections). Control mice received phosphate buffered saline (PBS) injections. The vaccinated mice received 1 mg of neutralizing anti-IFNγ (XMG6) and/or anti-TNFα (XT22) monoclonal antibodies (mAbs) on days –1, 3 and 7. Mice were subsequently assayed for delayed type hypersensitivity (DTH) and for mitogen and alloantigen stimulation of splenocytes as described below.

The mitogen and alloantigen stimulation of splenocytes assay was performed as follows: In vitro mitogenic stimulation of splenocytes with 2.5 mg/ml Con A or 100 U/ml rmIL-12 was performed as described [Kurzawa, cited above]. Proliferative responses to allogeneic antigens (mixed lymphocyte reaction, MLR) was measured when splenocytes from the mice were stimulated with $10^5$ mitomycin treated A/J splenocytes. Splenocyte fractionation was performed by allowing $10^5$ splenocytes to adhere for 90 minutes in 96 well plates, after which the nonadherent cells were removed and cocultured with adherent cells from different wells for assay. When added, antibodies (XMG6 for IFNγ, XT22 for TNFα, AE5 for IL-10 and C17.8 for IL-12 ) were used at 10 mg/ml final concentration. After 72 hours exposure to mitogen, cultures were pulsed with 1 $\mu$Ci$^3$H-thymidine for 16 hours, cells were harvested and $^3$H incorporation was measured by scintillation counting. Supernatants from cultures assayed for IFNγ by radioimmunoassay (RIA) (using antibodies AN18 and XMG6 [Wysocka, M. et al. 1995 *Eur. J. Immunol.* 25:672] were harvested 24 or 72 hours after stimulation.

The DTH assessment was performed as follows: For assessment of allogeneic DTH responses, mice were injected with 50 $\mu$l PBS containing $10^6$ irradiated SCK cells in the right footpad and with 50 $\mu$l PBS in the left footpad. Footpad thickness measurements were taken just before injection and 24 hours later using a Starrett pocket gauge (Athol, Mass.). Data are presented as the difference in footpad swelling induced by SCK cells and by PBS.

The results of these experiments were as follows: Recombinant murine (rm)IL-12 suppressed in vivo DTH and in vitro mitogenic and alloproliferative responses. XMG6 (anti-IFNγ) completely restored DTH responses, XT22 (anti-TNFα) only partially restored responses, and XMG6+ XT22 restored responses no better than XMG6 alone (data not shown). Thus, IFNγ is crucial for rmIL-12 suppression of immune responses and the role of TNFα is less certain.

B. The role of these cytokines was examined more definitively by testing the effect of rmIL-12 on alloimmunization in mice genetically deficient for these cytokines or their receptors.

C57BL/6 mice genetically deficient for IFNγ (IFNγ$^{-/-}$) and wild-type C57BL/6 mice were vaccinated with $10^6$ irradiated HKB cells and given 500 ng rmIL-12 or phosphate buffered saline (PBS) on days 0–4 and 7–11 or left unvaccinated. They were challenged with $10^6$ irradiated SCK cells in the right foot, with PBS control injection in the left foot on day 12. The DTH responses were measured as described above in Part A.

The results of this experiment, illustrated in FIG. 1A, demonstrate that a course of rmIL-12 suppressed DTH responses to background levels in wild-type mice but had no suppressive effect in the IFNγ$^{-/-}$ mice. In a companion experiment, C57BL/6×SV129 mice deficient for the IFNγ receptor and vaccinated with HKB cells displayed similar results: rmIL-12 suppressed DTH responses in control but not IFNγR1$^{-/-}$ mice (data not shown). From these results, IFNγ was shown to be crucial for rmIL-12 induced immunosuppression.

C. To examine the role of TNFα, SV129×C57BL/6 mice deficient for both p55 and p75 TNF receptors (TNFR$^{-/-}$ mice) and control mice were vaccinated with $10^6$ irradiated HKB cells and given 500 ng IL-12 or PBS on days 0–4 and 7–11. DTH assessment was performed on day 12, as described above in Part A.

Figure 1B:
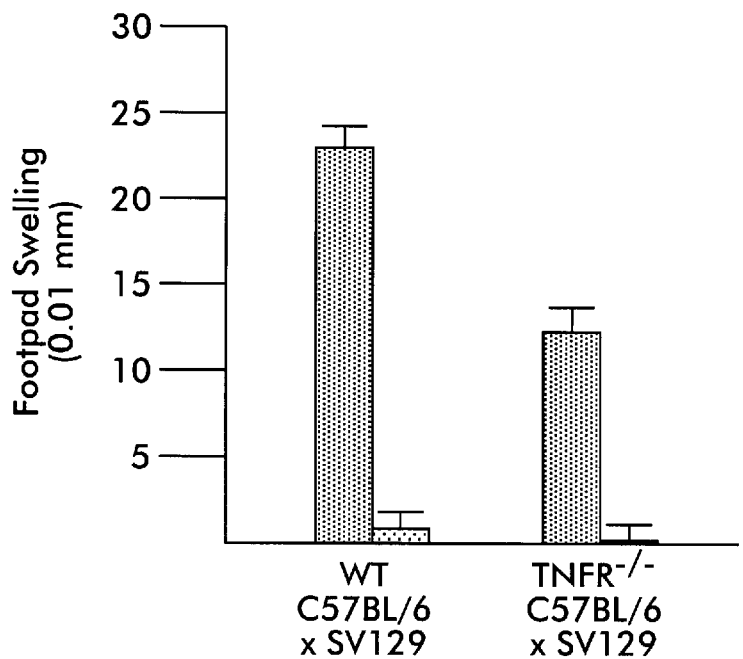
FIG. 1B is a bar graph which reports mean footpad swelling (+S.E.) for SV129×C57BL/6 mice deficient for both p55 and p75 TNF receptors and control mice which are (a) vaccinated with HKB cells and given IL-12 (gray bars) or (b) vaccinated with HKB cells and given PBS (black bars) on days 0–4 and 7–11. Delayed type hypersensitivity (DTH) assessment was performed on day 12.

The results are illustrated in FIG. 1B. HKB-vaccinated TNFR$^{-/-}$ mice treated with rmIL-12 had depressed DTH responses like wild-type C57BL/6×SV129 mice, indicating that TNFα responses were dispensable for rmIL-12 immune suppression. However, DTH responses without rmIL-12 were lower in the TNFR$^{-/-}$ mice, suggesting that TNFα responses might be necessary for maximal responses.

D. In earlier studies of the inventor, suppression of in vitro splenocyte mitogenic responses correlated well with suppression of in vivo immune responses. This correlation held up in studies of IFNγ$^{-/-}$ and TNFR$^{-/-}$ mice: Con A, IL-12 and allogeneic stimulation of splenocytes from rmIL-12 treated IFNγ$^{-/-}$ mice, as described above in Part A resulted in normal proliferative responses, while responses of splenocytes from rmIL-12-treated TNFR$^{-/-}$ mice were suppressed (data not shown).

EXAMPLE 2

Adherent Cells Mediate IL-12 -Induced Suppression of Splenocyte Mitogenesis

The following experiments identified the cell population responsible for the suppressed splenocyte mitogenic responses.

A. Splenocytes from rmIL-12- and PBS-treated C57BL/6 mice were fractioned by adherence to 96 well plastic plates for 90 minutes. The cells were reconstituted in various combinations of adherent and nonadherent cells by overlaying nonadherent cells on the adherent cells. These cocultures were then stimulated with either 2.5 $\mu$g/ml Con A, 100 U/ml IL-12, or $10^5$ mitomycin C treated A/J (H-2A) splenocytes, as described in the mitogen/alloantigen assay of Example 1.

Figure 2:
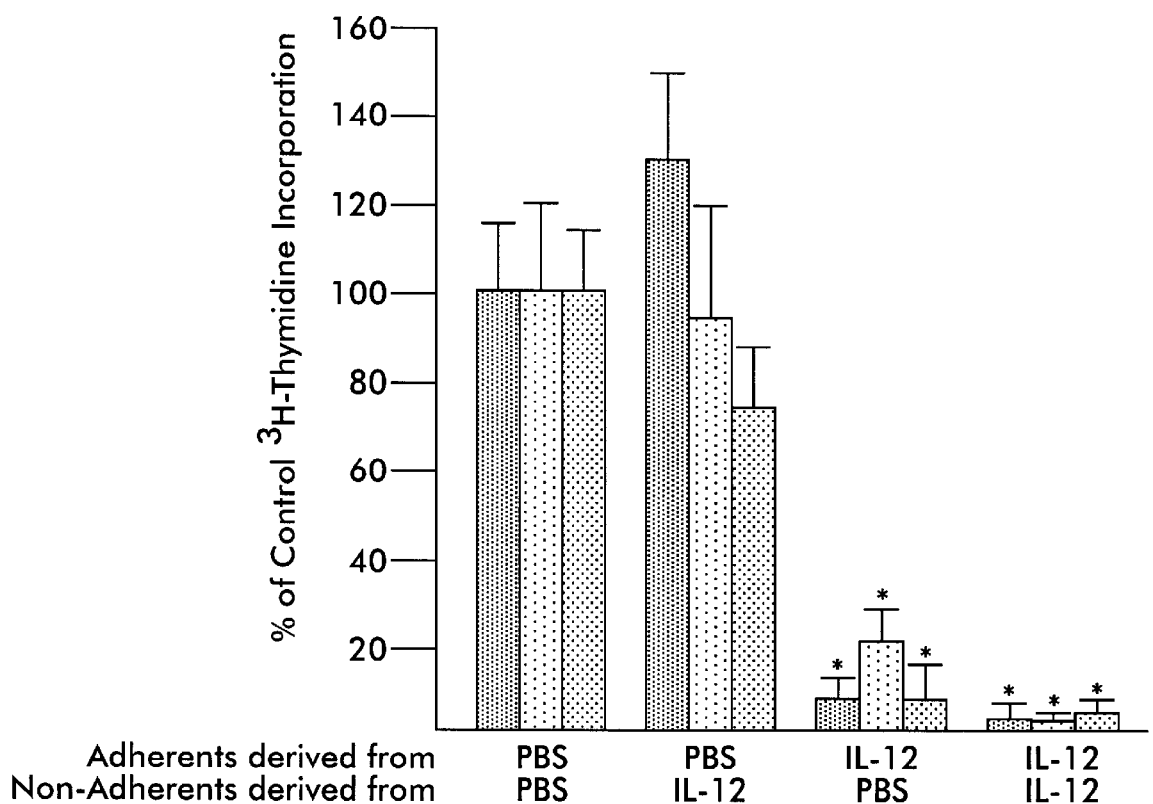
FIG. 2 is a graph illustrating percentage (+S.E.) of stimulation measured as tritiated thymidine incorporation for splenocytes from rmIL-12-treated, and PBS-treated, C57BL/6 mice which were allowed to adhere to 96 well plates for 90 minutes, overlaid with nonadherent cells and stimulated with either 2.5 μg/ml ConconavalinA (Con A; black bars), 100 U/ml IL-12 (hatched bars), or $10^5$ mitomycin C treated A/J ($H-2^a$) splenocytes (stippled bars). Cultures of adherent and nonadherent cells from spleens of PBS-treated mice are reported. Coculture data are from triplicate determinations and are significantly different from control mixtures (adherent and nonadherent cells from PBS treated mice, $p<0.05$) where indicated (*).

The data reported in FIG. 2 are from one of five experiments that produced similar results and are shown as the percentage (+S.E.) of stimulation elicited in cultures of adherent and nonadherent cells from spleens of PBS-treated mice, with the exception of the data indicated on the graph by an asterisk. The latter data are from triplicate determinations and are significantly different from control mixtures (adherent and nonadherent cells from PBS treated mice, p<0.05). As expected, cultures of adherent and nonadherent splenocytes from rmIL-12 treated mice had suppressed mitogenic responses compared to cultures of adherent and nonadherent cells from PBS-treated mice. Nonadherent cells from rmIL-12 treated mice cocultured with adherent cells from PBS-treated mice had normal mitogenic responses, indicating that mitogenesis of T cells from rmIL-12 treated mice is not intrinsically or irreversibly defective.

When nonadherent cells from control mice were mixed with adherent cells from rmIL-12 treated mice, proliferative responses were severely impaired, whether the stimulus was Con A, IL-12 or alloantigen. These results indicate that T cells from rmIL-12 treated mice can respond to mitogens and generate an antigen-specific mitogenic response in the presence of adherent cells from normal mice and that adherent cells are largely responsible for the defect following rmIL-12 therapy.

IFNγ was readily detected by radioimmunoassay (RIA) in cocultures of adherent cells from rmIL-12-treated mice and nonadherent cells from PBS-treated mice at both 24 hours and 72 hours after stimulation with Con A, IL-12 or alloantigen (data not shown).

B. Cocultures were established from splenic adherent and nonadherent cells of PBS-treated mice or from the adherent cells of rmIL-12-treated mice and nonadherent cells of PBS-treated mice. Antibodies XMG6 (to IFNγ), XT22 (to TNFα), AE5 (to IL-10) and C17.8 (to IL-12 ) were added to a final concentration of 10 mg/ml in cocultures containing adherent cells from spleen of rmIL-12-treated mice, also according to the assay described in Example 1.

Figure 3A:
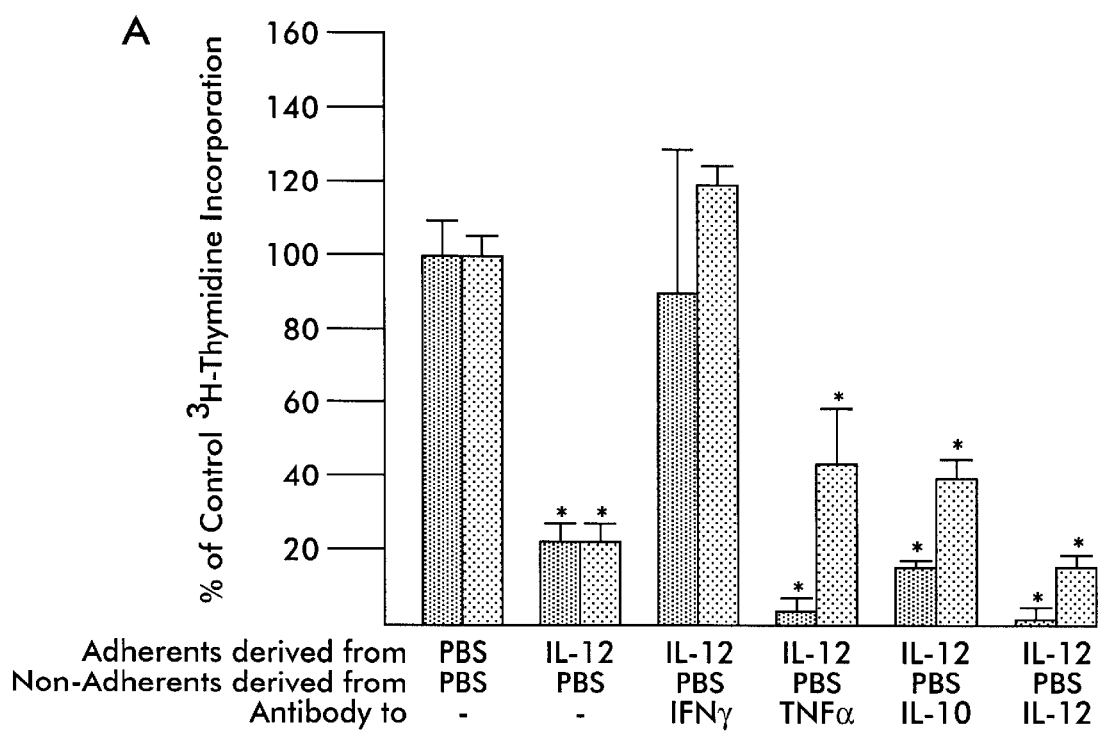
FIG. 3A is a bar graph illustrating percentage (+S.E.) of stimulation measured as tritiated thymidine incorporation for cocultures established from splenic adherent and nonadherent cells of PBS-treated mice or from the adherent cells of rmIL-12-treated mice and nonadherent cells of PBS-treated mice. Antibodies XMG6 (to IFNγ), XT22 (to TNFα), AE5 (to IL-10) and C17.8 (to IL-12) were added to cocultures containing adherent cells from spleen of rmIL-12-treated mice. Data from Con A- (black bars) and IL-12- (hatched bars) stimulated cultures are from triplicate determinations and are significantly different from control cocultures ($p<0.05$) where indicated (*).

The results of this experiment, reported in FIG. 3A, from Con A- and IL-12-stimulated cultures are from triplicate determinations and are significantly different from control cocultures (p<0.05) where indicated (*). This data demonstrates that the addition of anti-IFNγ antibody to these cocultures restored mitogenic responses, while addition of antibodies to IL-12, IL-10 or TNFα had little effect. These antibodies did not suppress mitogenic responses in cocultures containing adherent and nonadherent splenocytes from PBS-treated mice (data not shown), indicating that they had no intrinsic suppressive effects that shrouded any beneficial effects of cytokine neutralization. These data support the results of in vivo experiments showing a critical role for IFNγ in rmIL-12 immune suppression. Adherent cells are important for rmIL-12 suppression of in vitro mitogenic and immunological responses and IFNγ is necessary for this effect.

EXAMPLE 3

Adherent Cell-derived Nitric Oxide Inhibits Proliferative and Immune Responses

The following experiments demonstrate that IFNγ induced nitric oxide (NO) from activated macrophages mediates rmIL-12 induced immunosuppression.

Cocultures were established from splenic adherent and nonadherent cells of PBS-treated mice or from the adherent cells of rmIL-12-treated mice and nonadherent cells of PBS-treated mice. Antibodies XMG6 (to IFNγ), XT22 (to TNFα), AE5 (to IL-10) and C17.8 (to IL-12) were added to a final concentration of 10 mg/ml in cocultures containing adherent cells from spleen of rmIL-12-treated mice. An inhibitor of inducible nitric oxide synthase (iNOS), L-NMMA (Sigma), was added to cocultures of adherent cells from rmIL-12 treated mice and nonadherent cells from control mice at a final concentration of 500 mM. Alternatively, D-NMMA (Sigma), a noninhibitory isoform of L-NMMA, was added to other cocultures as a control.

NO production was measured as nitrite concentration in stimulated cell supernatants by the Greiss assay [Green, L. C. et al, *Anal. Biochem* 126:131 (1982)]. Supernatant (100 μl) was added to 96 well plates; 100 μl of a 1:1 mixture of 1% sulfanilamide dihydrochloride in 2.5% $H_3PO_4$ and 0.1% naphthylethylenediamine dihydrochloride in 2.5% $H_3PO_4$ was then added to samples. Plates were incubated at room temperature for 10 minutes and A540 was determined using a microplate reader with reference to sodium nitrite standard curves. S-nitroso-N-acetyl-penillamine (SNAP, Sigma), an NO donor, was used as a acellular source of NO and was added to splenocytes from HKB-vaccinated C57BL/6 mice.

Figure 3B:
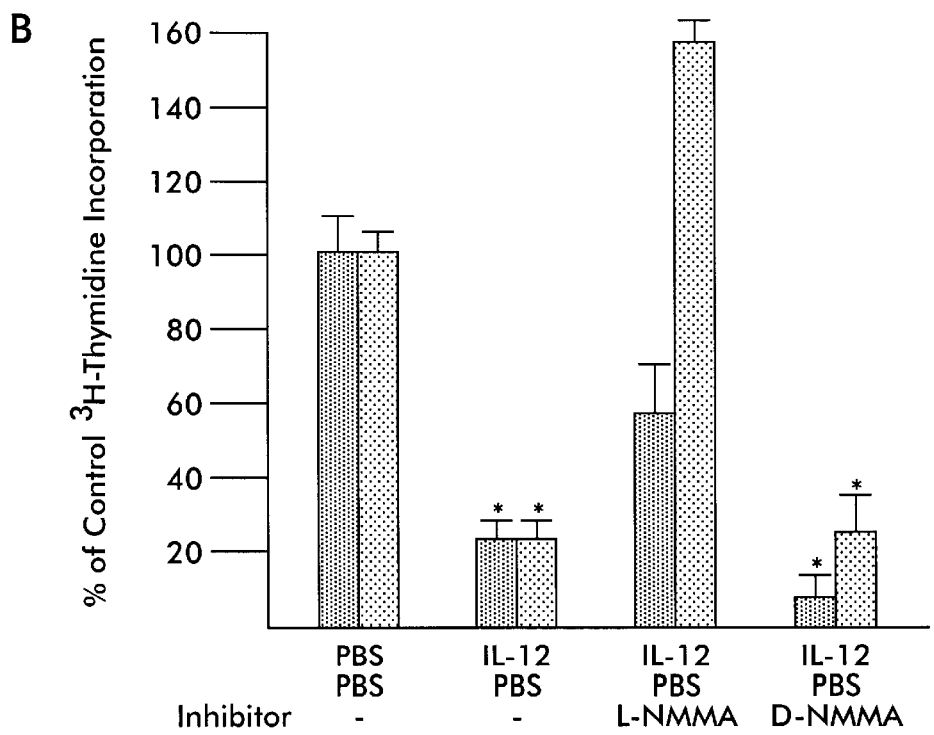
FIG. 3B is a bar graph of the same experiment as described for FIG. 3A, except that $N^G$-monomethyl-L-arginine (L-NMMA), a nitric oxide synthase inhibitor, and $N^G$-monomethyl-D-arginine (D-NMMA), the inactive isoform, were added to the coculture containing adherent cells from rmIL-12-treated mice. Data from Con A- (black bars) and IL-12- (hatched bars) stimulated cultures are from triplicate determinations and are significantly different from control cocultures ($p<0.05$) where indicated (*).

The results of this experiment are reported in FIG. 3B, in which data from Con A- and IL-12-stimulated cultures are from triplicate determinations and are shown to be significantly different from control cocultures (p<0.05) where indicated (*) The NO inhibitor L-NMMA reduced NO levels in the culture supernatant by 58% and 94% in two independent measurements and restored mitogenesis, when compared to addition of D-NMMA. If secreted NO is responsible for suppression of mitogenesis, an acellular source of NO should have a similar effect. Cultures with NO levels as low as 2.6–3.5 mM from the addition of SNAP inhibited mitogenic responses 83–98%. Together, these data indicate that adherent splenocytes (probably macrophages) activated by rmIL-12 treatment to secrete NO are responsible for impaired T cell mitogenic responses.

The ability of an iNOS inhibitor to reverse rmIL-12-induced suppression of mitogenesis in vitro suggested that mice lacking iNOS might be resistant to the immunosuppressive effects of rmIL-12. iNOS-/- and wild-type C57BL/6 mice were vaccinated with irradiated HKB cells and given a course of either rmIL-12 or PBS injections, as described in the experiments above. Footpad injections for DTH assessment were performed on day 12 as described above in the DTH assay. Swelling 24 hours later is presented as the mean (+S.E.) from 3 mice in each treatment group in FIG. 4A. Mitogenic and allogeneic stimulation of splenocytes were also performed as described in Example 1, and these results reported in FIG. 4B.

From the data in FIG. 4A, iNOS$^{-/-}$ mice receiving rmIL-12 had DTH responses that were at least as great as those of PBS-treated iNOS$^{-/-}$ and wild-type mice that were substantially higher than those of wild-type mice given rmIL-12. Although rmIL-12 induced splenomegaly in iNOS$^{-/-}$ mice like wild-type mice [Car, B. D. et al. 1995 *Am. J. Path.* 147:1693], their splenocytes had proliferative responses like those of splenocytes from control mice after in vitro stimulation with mitogens or alloantigens (FIG. 4B).

Together, these data show that macrophage-derived NO is essential for rmIL-12-induced immunosuppression while rmIL-12-induced splenomegaly and associated pathological changes are not.

EXAMPLE 4

IL-12-Vaccine Adjuvant Activity is More Apparent when NO Generation is Inhibited RmIL-12 does not suppress allogeneic responses in iNOS$^{-/-}$ mice. Thus, whether iNOS inhibitors would prevent immunosuppression in mice given rmIL-12 during tumor cell vaccination was demonstrated as follows. Previously, the inventors showed that vaccinating A/J mice with irradiated SCK tumor cells engineered to secrete GM-CSF (SCK.GM cells) was highly protective, but the administration of rmIL-12 abrogated protection two weeks after vaccination (but had no deleterious effect four weeks after vaccination) [Kurzawa et al, *Cancer Res,* 58: 491(1998)].

The following experiments demonstrated that inhibition of iNOS function reverses suppression of immunological protection.

A. Female A/J mice were vaccinated with $10^6$ irradiated SCK.GM cells suspended in PBS at $10^7$ trypan blue-excluding cells/ml. Cells were irradiated with 6000 rads from a $^{137}$Cs source, and mice were vaccinated with $10^6$ cells s.c. (day 0). Mice were given either rmIL-12 (Genetics Institute, Andover, Mass.) injected intraperitoneally (ip) 250 ng/day on days 0–4 and 7–11 (10 injections), or rmIL-12+ L-NAME (an inhibitor of iNOS that acts similarly to L-NMMA) injected at the same dosage and regimen, or rmIL-12 and D-NAME (the inactive isoform) injected at the same dosage and regimen, while control mice received PBS injections. Vaccinated and naive A/J mice were challenged fourteen days after vaccination with $2.5 \times 10^4$ trypan blue-excluding SCK cells in the opposite flank to assay for the presence of tumor immunity. Tumorigenesis was scored daily.

Figure 5:
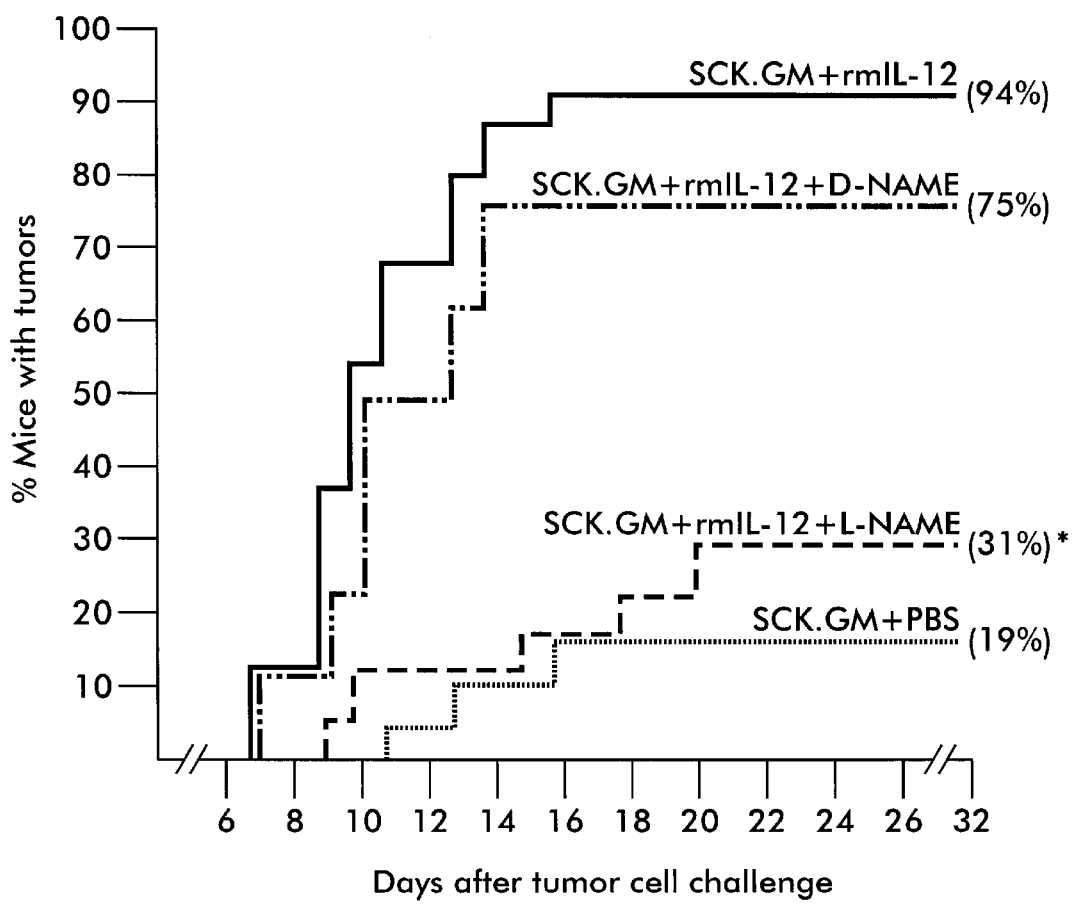
FIG. 5 is a graph indicating the percentage of mice with tumors for female A/J mice vaccinated with SCK.GM cells and given either PBS (solid gray lines), or rmIL-12 (solid black lines), or rmIL-12+$N^{\omega10\gamma}$-nitro-L-arginine methyl ester (L-NAME) (hatched black lines) or rmIL-12 and $N^\omega$-nitro-D-arginine methyl ester (D-NAME) (double dashed black lines) on days 0–4 and 7–11. Mice were challenged fourteen days after vaccination with SCK cells in the opposite flank and tumorigenesis scored daily. The (*) designates statistical differences at $p<0.05$ for rmIL-12 and L-NAME treated mice vs. rmIL-12 and D-NAME treated mice and vs. rmIL-12 treated mice. Data are compiled from two separate experiments that produced consistent results (15–17 mice per group total).

The results are indicated in the graph of FIG. 5, in which the difference in tumorigenesis between rmIL-12 treated mice given L-NAME vs. either D-NAME or nothing is statistically significant at $p<0.05$ (*). Data are compiled from two separate experiments that produced consistent results (15–17 mice per group total). As expected, SCK.GM vaccination protected the great majority of mice from tumor cell challenge two weeks after vaccination, and rmIL-12 severely impaired this protection. L-NAME but not D-NAME prevented this impairment (75% developed tumors). In mice not treated with rmIL-12, L-NAME and D-NAME had no effect on SCK.GM-induced protection (data not shown), showing that L-NAME acts by preventing rmIL-12 suppression of SCK.GM vaccine efficacy.

rmIL-12 also impairs tumor protection in A/J mice with established SCK immunity if it is given just prior to tumor cell rechallenge [Kurzawa, cited above]. L-NAME but not D-NAME given with rmIL-12 therapy prevented this impairment of immune rejection: only 25% of rmIL-12 treated mice given L-NAME developed tumors, whereas 75% of rmIL-12-treated mice given D-NAME developed tumors (data not shown). Thus, L-NAME prevents rmIL-12 suppression of established antitumor immune responses. In these studies, levels of NO were not consistently measurable in mice given rmIL-12, so lower levels in mice also given L-NAME could not be demonstrated.

B. Vaccination of A/J mice with irradiated wild-type SCK cells protected only about 10% of mice from a tumor cell challenge, i.e. SCK cells are intrinsically poorly immunogenic. Giving rmIL-12 with vaccination did not improve protection when mice were challenged 14 days after vaccination, but did improve protection when they were challenged at 28 days [Kurzawa, cited above]. Since an iNOS inhibitor prevented transient immunosuppression by rmIL-12, the following experiment was performed to determine whether its use might reveal rmIL-12's effectiveness as a vaccine adjuvant at the earlier time point.

Female A/J mice (8 mice per group) were vaccinated with $10^6$ irradiated SCK cells and received either PBS, rmIL-12, rmIL-12+L-NAME or rmIL-12 and D-NAME on days 0–4 and 7–11. Mice were challenged fourteen days after vaccination with $2.5 \times 10^4$ SCK cells in the opposite flank. Tumorigenesis was scored daily, as described above.

Figure 6:
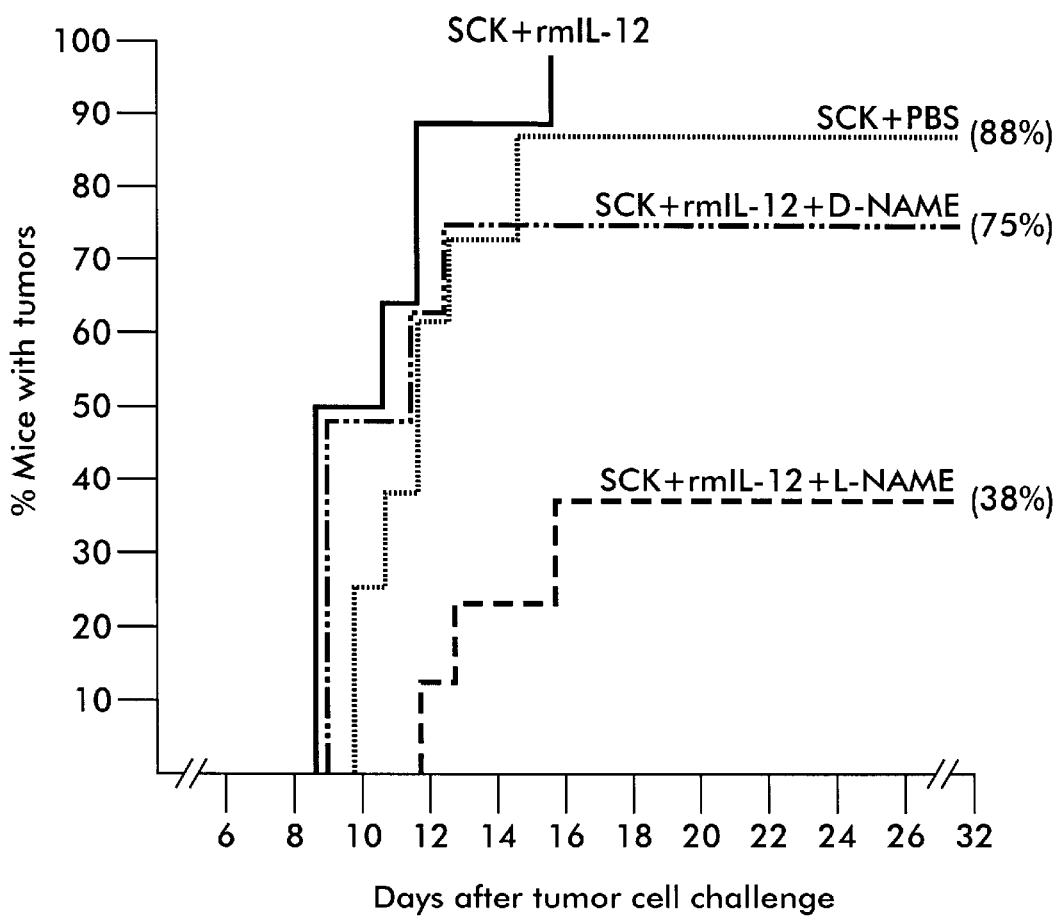
FIG. 6 is a graph reporting percentage of mice with tumors for female A/J mice (8 mice per group) vaccinated with SCK cells and treated with either PBS (solid gray lines), rmIL-12 (solid black lines), rmIL-12+L-NAME (hatched black lines) or rmIL-12+D-NAME (double dashed black lines) on days 0–4 and 7–11. Mice were challenged fourteen days after vaccination with SCK cells in the opposite flank. Tumorigenesis was scored daily.

The results are demonstrated in FIG. 6. Only 38% of mice given L-NAME with irradiated SCK cells and rmIL-12 developed tumors when they were challenged on day 14, whereas 75% of mice given D-NAME developed tumors. This indicated that rmIL-12 improves SCK cell vaccine efficacy markedly and rapidly, but that the improvement at day 14 was obscured by rmIL-12's immunosuppressive effect. The level of protection with L-NAME at 14 days (62%) was similar to the level of protection seen at 28 days in SCK-vaccinated mice given rmIL-12 alone (75%) or rmIL-12 with L-NAME (50%) of D-NAME (50%), indicating that use of L-NAME did not impair long-term protection afforded by rmIL-12 and SCK vaccination.

C. Use of an iNOS inhibitor to alleviate rmIL-12 immune suppression would be problematic if it reduces the antitumor efficacy of the cytokine- an important consideration since the antitumor effects of rmIL-12 are diverse, and some of which are not immunological [Voest, E. E. et al, *J. Natl. Cancer Inst.*, 87:5813 (1995)]. Thus, the effect of L-NAME was tested on the antitumor activity of rmIL-12 against SCK tumors.

Female A/J mice were injected with $2.5 \times 10^4$ SCK cells and either PBS, rmIL-12, rmIL-12+L-NAME or rmIL-12 and D-NAME on days 0–4 and 7–11. Tumorigenesis was scored daily, as described above.

Figure 7:
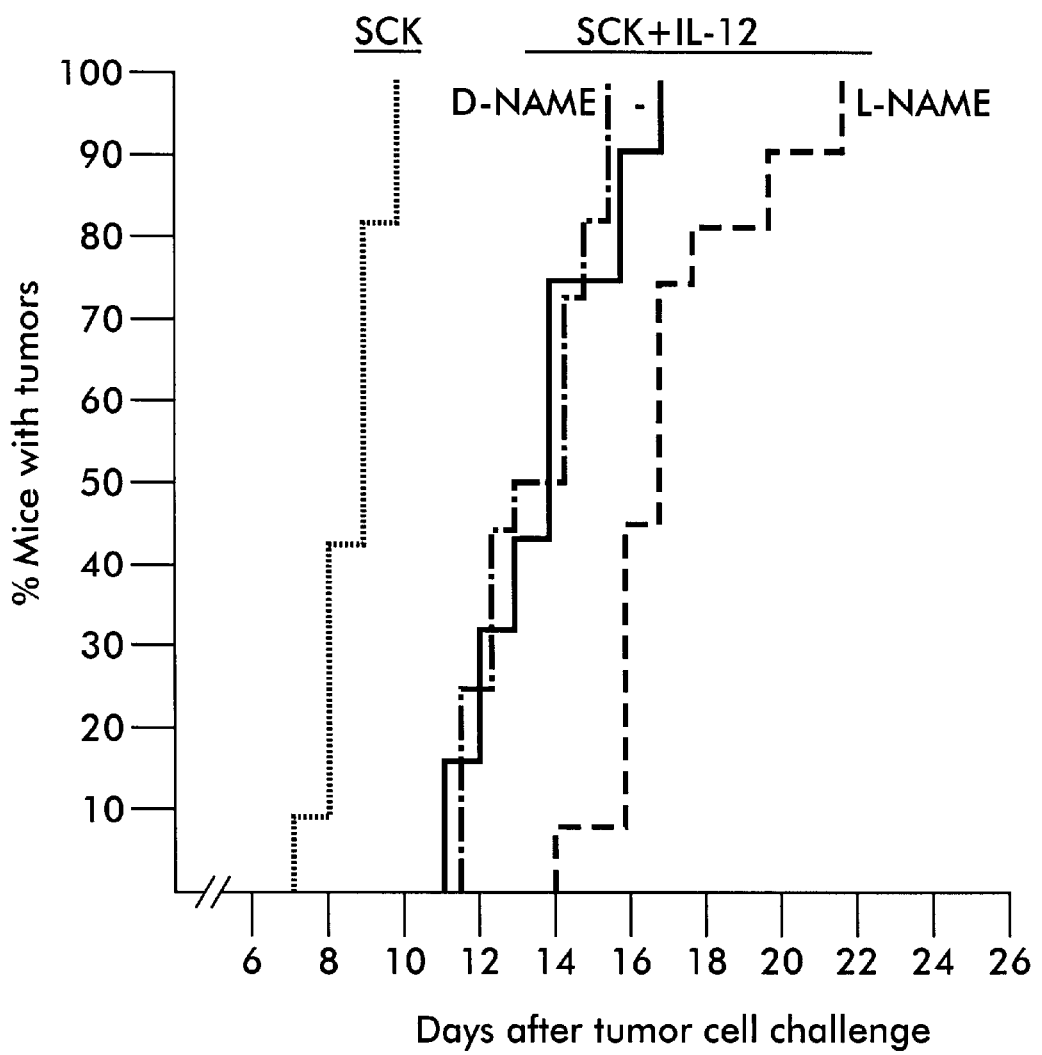
FIG. 7 is a graph reporting percentage of mice with tumors for female A/J mice injected with SCK cells and given either PBS (solid gray lines), rmIL-12 (solid black lines), rmIL-12+L-NAME (hatched black lines) or rmIL-12 and D-NAME (double dashed black lines) on days 0–4 and 7–11. Tumorigenesis was scored daily. Data are compiled from two separate experiments that produced consistent results (11–12 mice per group total).

The results of this experiment are reported in FIG. 7 and are compiled from two separate experiments that produced consistent results (11–12 mice per group total). Similar to what was seen in the past [Coughlin, C.M. et al., *Cancer Res.* 55:4980 (1995)], rmIL-12 injections started on the day of SCK cell injection delayed tumor appearance by about 5 days (FIG. 7 shows medians of 9 days to tumor appearance without rmIL-12 and 14 days to tumor appearance with rmIL-12). Mice given L-NAME with their rmIL-12 developed tumors after a median of 17 days which was 8 days later than in untreated mice and 3 days later than in mice given rmIL-12 alone or with D-NAME. L-NAME given without rmIL-12 had no effect on SCK tumorigenesis (data not shown).

This experiment indicated that inhibition of iNOS function potentiates rmIL-12 induced delay of SCK tumorigenesis.

All published documents are incorporated by reference herein. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for enhancing the adjuvant effect of IL-12 comprising: co-administering to a mammalian patient said IL-12, a vaccine antigen, and an effective amount of at least one agent selected from the group consisting of a nitric oxide inhibiting agent and a nitric oxide neutralizing agent.

2. The method according to claim 1 wherein said agent is an agent that inhibits or reduces the synthesis of nitric oxide in vivo.

3. The method according to claim 1 wherein said agent is an agent that breaks down, absorbs, metabolizes or eliminates nitric oxide in vivo.

4. The method according to claim 1 wherein said co-administration comprises simultaneously administering said agent with said IL-12 and said antigen.

5. The method according to claim 1 wherein said co-administration comprises sequentially administering said agent, said IL-12 and said antigen, in any order.

6. The method according to claim 3 wherein said co-administration comprises administering said IL-12 before said agent.

7. The method according to claim 2 wherein said agent inhibiting nitric oxide generation is an inhibitor of nitric oxide synthase.

8. The method according to claim 7 wherein said agent is specific for inducible nitric oxide synthase.

9. The method according to claim 2 wherein said agent is selected from the group consisting of L-$N^G$ monomethyl arginine (L-NMMA), L-$N^G$ nitroarginine (L-NORAG), L-$N^G$ nitroarginine methylester (L-NAME), L-$N^G$ nitroarginine p-nitroanilide (L-NAPNA), L-$N^G$ aminoarginine (L-NAA), L-$N^G$ cyclopropylarginine, L-$N^G$ allylarginine, asymmetric L-$N^G N^G$ dimethylarginine (L-ADMA), L-$N^\omega$ iminoethyl ornithine (L-NIO), 7-nitro indazole (7-NI), 2,7 dinitro indazole, 3-bromo 7-nitro indazole, aminoguanidine, N,N'-diaminoguanidine, dimethylguanidine, diphenyleneiodonium, iodoniumdiphenyl, di-2-thienyliodonium, chlorpromazine, trifluoperazine, pimozide, clozapine, calmidazolium, 2,4 diamino-6-hydroxypyrimidine, methotrexate, N-acetyl-5-hydroxytryptamine, miconazole, ketoconazole, clotrimazole, imidazole, 1-, 2- and 4-phenylimidazole, methylene blue, NO, carbon monoxide, ebselen, phencyclidine, and antineoplastic agents (doxorubicin, aclarubicin).

10. The method according to claim 9 wherein said agent is L-NAME.

11. The method according to claim 9 wherein said agent is L-NMMA.

12. The method according to claim 3 wherein said agent is a nitric oxide scavenger.

13. The method according to claim 12 wherein said scavenger is selected from the group consisting of N-acetyl cysteine, pyrrolidine dithiocarbamate, and hemoglobin.

14. The method according to claim 1 wherein said vaccine antigen is a mammalian tumor cell antigen.

15. The method according to claim 1 wherein said vaccine antigen is a pathogenic antigen selected from the group consisting of bacterial antigens, viral antigens, and parasitic antigens.

16. An adjuvant composition comprising an effective adjuvanting amount of IL-12 and an effective amount of at least one agent selected from the group consisting of a nitric oxide inhibiting agent and a nitric oxide neutralizing agent, in a pharmaceutically acceptable carrier.

17. A vaccine composition comprising an effective adjuvanting amount of IL-12, an effective amount of at least one agent selected from the group consisting of a nitric oxide inhibiting agent and a nitric oxide neutralizing agent, and an effective protective amount of a vaccine antigen in a pharmaceutically acceptable carrier.

18. A method of preparing an adjuvant composition comprising combining in a pharmaceutically acceptable carrier an effective amount of a vaccine antigen, and an effective adjuvanting amount of IL-12 and an effective amount of at least one agent selected from the group consisting of a nitric oxide inhibiting agent and a nitric oxide neutralizing agent.

* * * * *

UNITED STATES PATENT AND TRADEMARK OFFICE
CERTIFICATE OF CORRECTION

PATENT NO. : 6,375,944 B1
DATED : April 23, 2002
INVENTOR(S) : Giorgio Trinchieri et al.

It is certified that error appears in the above-identified patent and that said Letters Patent is hereby corrected as shown below:

Column 1,
Line 62, replace "EI-12" with -- IL-12 --.

Column 4,
Line 17, replace "12+N$^{x107}$" with -- 12+N$^w$ --.

Column 5,
Line 4, replace "below." with -- below). --.
Line 48, replace "iNOS-/-" with -- iNOS$^{-/-}$ --.

Column 8,
Line 33, replace "[See," with -- See, --.
Line 38, replace "herein]." with -- herein. --.

Column 10,
Line 56, replace "haemorrhagic" with -- hemorrhagic --.

Column 11,
Line 19, replace "as" with -- a --.

Column 12,
Line 40, replace "TNFαp55 and" with -- TNFα p55 and --.
Line 56, replace "H," with -- H., --.

Column 13,
Line 31, replace "mycin treated A/J" with -- mycin C-treated A/J --.

UNITED STATES PATENT AND TRADEMARK OFFICE
CERTIFICATE OF CORRECTION

PATENT NO. : 6,375,944 B1
DATED : April 23, 2002
INVENTOR(S) : Giorgio Trinchieri et al.

It is certified that error appears in the above-identified patent and that said Letters Patent is hereby corrected as shown below:

Column 16,
Line 9, replace "a" with -- an --.

Column 17,
Line 35, replace "rmIL-12" with -- RmIL-12 --.

Signed and Sealed this

Eighth Day of October, 2002

Attest:

Attesting Officer

JAMES E. ROGAN
Director of the United States Patent and Trademark Office